United States Patent [19]

Tirtowidjojo et al.

[11] Patent Number: 5,504,266
[45] Date of Patent: Apr. 2, 1996

[54] PROCESS TO MAKE ALLYL CHLORIDE AND REACTOR USEFUL IN THAT PROCESS

[75] Inventors: Max M. Tirtowidjojo; Paul C. Beckett, both of Lake Jackson; John F. Baker, Freeport, all of Tex.

[73] Assignee: The Dow Chemical Company, Midland, Mich.

[21] Appl. No.: 449,635

[22] Filed: May 24, 1995

[51] Int. Cl.⁶ .................................................. C07C 17/16
[52] U.S. Cl. .................................................. 570/234
[58] Field of Search ............................................ 570/234

[56] References Cited

U.S. PATENT DOCUMENTS

| | | | |
|---|---|---|---|
| 2,643,272 | 6/1953 | Lacomble et al. | |
| 2,763,699 | 9/1956 | van Dijk et al. | |
| 3,054,831 | 9/1962 | Samples et al. | |
| 3,120,568 | 2/1964 | Brown | 570/234 |
| 3,472,902 | 10/1969 | Van Dijk | 570/234 |
| 3,865,886 | 2/1975 | Schindler et al. | 570/234 |
| 4,319,062 | 3/1982 | Boozalis et al. | 570/234 |
| 5,367,105 | 11/1994 | Miyazaki et al. | 570/234 |

FOREIGN PATENT DOCUMENTS

| | | |
|---|---|---|
| 48-26732 | 8/1973 | Japan . |
| 60-252434 | 12/1985 | Japan . |
| 61-40232 | 2/1986 | Japan . |
| 136334 | 2/1987 | Poland . |
| 135873 | 5/1987 | Poland . |
| 761831 | 11/1956 | United Kingdom . |
| 765764 | 1/1957 | United Kingdom . |
| 901680 | 10/1960 | United Kingdom . |

*Primary Examiner*—Alan Siegel

[57] ABSTRACT

Allyl halide is produced in high yields and purity with minimal carbon formation using a process of: (1) initially reacting propylene and molecular halogen in a molar ratio of at least about 2.5:1 in a "continuously stirred tank reactor" (CSTR) zone under conditions suitable to provide a reaction temperature of about 400° C. to 525° C. to partially convert propylene and chlorine into allyl chloride; and (2) feeding an effluent from Step (1) into a plug-flow reactor zone where the reaction is continued at a temperature of about 400° C. to 525° C. until essentially all of the chlorine is consumed. A preferred reactor for the process contains: (1) a spherical, egg-shaped or oval reactor zone; (2) a tubular reactor zone attached to the spherical, egg-shaped or oval reactor zone; (3) one or more inlets for injecting gaseous reagents into the spherical, oval or egg-shaped reactor zone; and (4) one or more outlets from the tubular reactor zone for withdrawing a gaseous product.

14 Claims, 2 Drawing Sheets

PROCESS TO MAKE ALLYL CHLORIDE AND REACTOR USEFUL IN THAT PROCESS

BACKGROUND OF THE INVENTION

The present invention relates to gaseous halogenation reactions and reactors useful in those reactions.

It is well known to react propylene and chlorine in a vapor phase at high temperatures to make a mixture of products which contain predominantly allyl chloride. See, for example, Samples et al., U.S. Pat. No. 3,054,831 (Sep. 18, 1962), which is incorporated herein by reference. In such reactions, propylene and chlorine react at a temperature of 400° C. to 500° C. The molar ratio of propylene to chlorine in the reactor is usually between about 3:1 and about 5:1. The conversion of chlorine is usually about 100 percent, and the conversion of propylene is usually about 20 to 35 percent.

After the propylene is separated from the reaction mixture, the reaction product usually contains about 70 to 80 weight percent allyl chloride with the remainder being predominantly a mixture of many different chlorinated alkanes and alkenes. The reaction also makes small amounts of carbon. The carbon builds up in the reactor over a period of time, until the reactor must be shut down for cleaning.

The mixture of products is temperature dependent. Temperatures below about 400° C. favor the formation of excessive dihalogenated by-products, whereas temperatures more than about 500° C. favor decomposition of allyl chloride to produce excessive carbon and other products. See, for example, Samples et al., supra, at column 1, lines 15–25; and British Patent Specification 761,831 (published Nov. 21, 1956) at column 1, lines 28–40. Therefore, temperature control is important in order to obtain a desirable mixture of products.

However, temperature control is difficult because the reaction is strongly exothermic. The reagent must be injected into the reactor at a temperature far below the desired reaction temperature or the heat of reaction will drive the temperature in the reactor too high. Even so, hot and cool spots may exist in the reactor which generate undesirably high levels of reaction by-products.

Several different methods of improved mixing in the reactor have been suggested to minimize temperature differences.

(1) Vandijk, U.S. Pat. No. 2,763,699 (published Sep. 18, 1956); British Patent Specification 761,831 (published Nov. 21, 1956); and British Patent Specification 765,764 (published Jan. 9, 1957), which are incorporated herein by reference, teach a variety of spherical, egg-shaped, oval and similar reactors which can be used to make allyl chloride. These spherical reactors are still susceptible to fouling from carbon. British Patent Specification 761,831 shows high yields of allyl chloride produced using a series of three spherical reactors. The series of three spherical reactors is inefficient because it is necessary to constantly cool and then reheat the reaction mixture as it passes from one reactor to the other. It is also particularly susceptible to fouling with carbon because carbon produced in the first reactors must pass through the narrow injectors and pipes of subsequent reactors.

(2) Samples et al., U.S. Pat. No. 3,054,831 teaches a complex injection system to encourage turbulence and mixing within the reactor.

(3) Yamamoto et al., Japanese Published Application 48-26732 (published Aug. 15, 1973) teaches a circular tubular reactor with baffles near the injector for reagents to encourage mixing.

(4) Spadlo et al., Polish Patent 136,334 (published Feb. 20, 1987) teaches to premix the reagents at low temperature before they are injected into the reactor.

All of these reactors are still susceptible to carbon formation. They must be shut down periodically for cleaning. If carbon formation were reduced, the reactor could run longer between shutdowns. What is needed is a reactor and/or process which is highly selective to allyl chloride and which produces very low levels of carbon without the need to continually heat and cool the reaction products.

SUMMARY OF THE INVENTION

One aspect of the present invention is a process to make allyl chloride comprising the steps of:

(1) partially reacting propylene and molecular halogen in a molar ratio of at least about 2.5:1 in a "continuously stirred tank reactor" (CSTR) zone under conditions suitable to provide a reaction temperature of about 400° C. to 525° C. to partially convert propylene and chlorine into allyl chloride; and (2) feeding an effluent from Step (1) into a plug-flow reactor zone where the reaction is continued at a temperature of about 400° C. to 525° C. until essentially all of the chlorine is consumed.

(For the purposes of application, the term "continuously stirred tank reactor" (CSTR) does not necessarily imply or exclude the presence of an impeller or other stirring mechanism. "CSTR" means that the zone is designed to create turbulence which minimizes temperature and reagent gradients in the CSTR zone.)

A second aspect of the present invention is a reactor vessel comprising:

(1) an approximately spherical, egg-shaped or oval reactor zone;

(2) a tubular reactor zone attached to the spherical, egg-shaped or oval reactor zone;

(3) one or more inlets for injecting gaseous reagents into the spherical, oval or egg-shaped reactor zone; and (4) one or more outlets from the tubular reactor zone for withdrawing a gaseous product.

The CSTR provides exceptional mixing to bring reagents quickly up to the desired temperature with a minimum of thermal gradients. On the other hand, we have discovered that CSTR, such as spherical reactors, are susceptible to excessive backmixing when they are the sole reactor used in the reaction. Excessive backmixing increases formation of carbon and further chlorination of allyl chloride to make dichlorinated side-products, because a portion of the product resides in the reactor too long.

In the present invention, the reaction is commenced in a continuous stirred tank reactor zone to obtain the good mixing, but the reaction mixture is moved into a plug-flow reactor before the reaction is completed to minimize by-product formation. The process of the present invention is useful to make allyl chloride in high purity with low by-product formation. The reactor of the present invention may be used in that process or in other processes which involve vapor phase reaction.

DETAILED DESCRIPTION OF THE INVENTION

Figure 1:
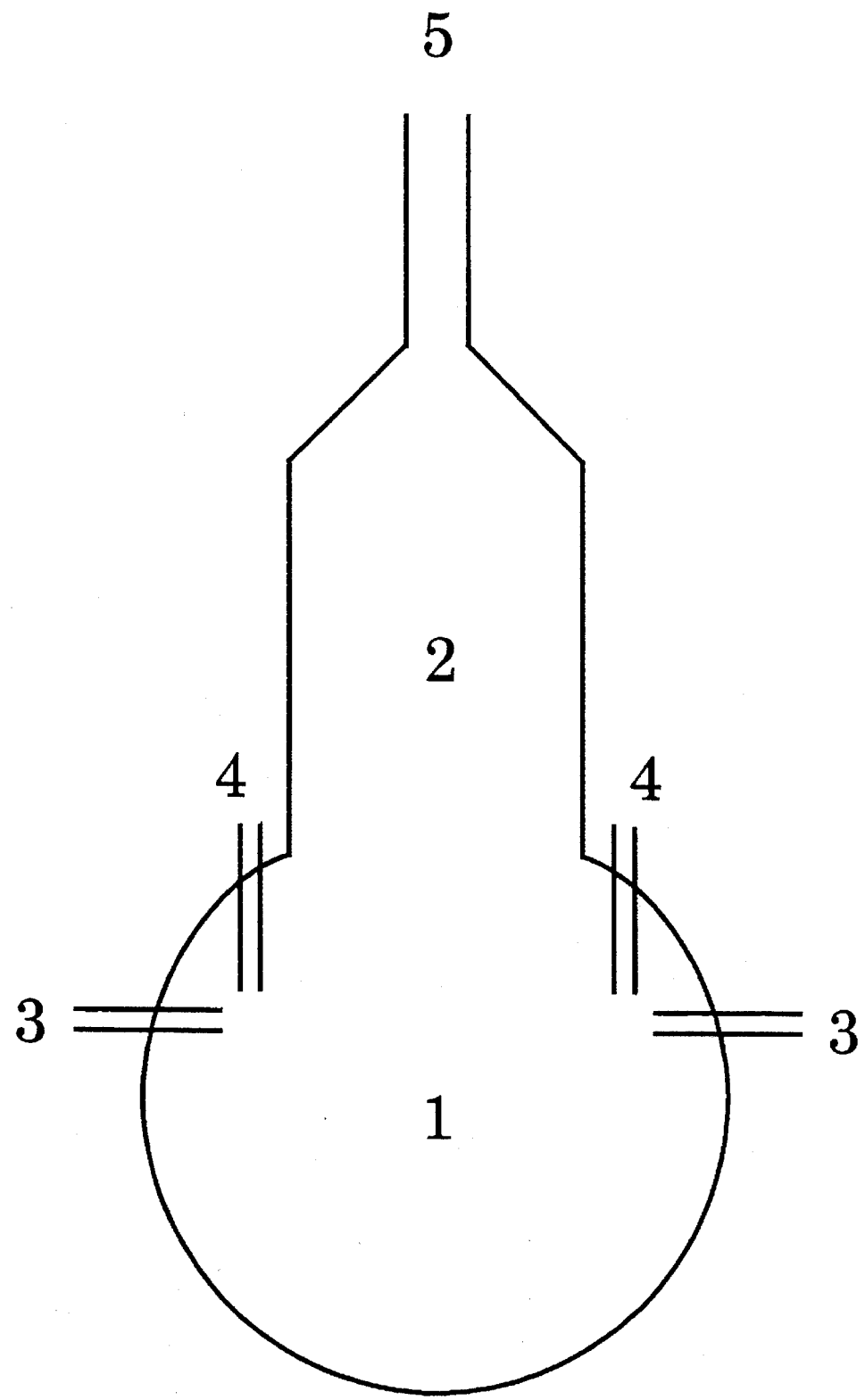
FIG. 1 illustrates a side view of a reactor containing: a spherical continually stirred tank reactor zone (1); a tubular plug-flow reactor zone (2); inlets for a first reagent (3); inlets for a second reagent (4); and an outlet for withdrawing products from the reactor (5).

In many respects, the process of the present invention follows the ordinary conditions for vapor phase halogenation of propylene to make allyl halides. Propylene and halogen are reacted together at an elevated temperature. The halogen is preferably chlorine or bromine, and is most preferably chlorine. The molar ratio of propylene to halogen fed into the reactor is at least about 2.5:1 and preferably at least about 3:1. The molar ratio of propylene to halogen fed into the reactor is preferably no more than about 5:1 and more preferably no more than about 4:1.

The temperature of the reactor is at least about 400° C., preferably at least about 425° C., more preferably at least about 450° C., and most preferably at least about 460° C. The temperature in the reactor is no more than about 525° C., preferably no more than about 500° C., and more preferably no more than about 480° C.

In most cases, it is desirable to preheat the propylene before feeding it into the reactor, particularly when the ratio of propylene to chlorine is high. The optimum preheating varies depending upon the reactor and the reaction conditions, and can readily be determined by a person of ordinary skill in the art through experimentation. The preheat should be just enough to maintain the temperature in the reactor at the desired temperature. If the reagents are preheated too much, the reactor temperature may rise too high, causing side reactions and carbon formation. Preferably, the propylene is heated to about 150° C. to 350° C. before it is injected into the reactor. Heat for this step is preferably recovered from effluent from the reactor.

The halogenation reaction takes place in two separate zones. In the first step, the reagents are fed into a CSTR zone. CSTRs are familiar to persons of ordinary skill in the art. The CSTR zone may be any reactor which has continual turbulence or mixing to quickly bring the reagents to reaction temperature and to minimize thermal and concentration gradients within the CSTR zone. Examples of CSTRs are described in the following references: Vandijk et al., U.S. Pat. No. 2,763,699 (Sep. 18, 1956); and G. Froment and K. Bischoff, *Chemical Reactor Analysis and Design* at 420 et seq. (J. Wiley & Sons 1979) which are incorporated herein by reference. The CSTR is preferably approximately spherical, egg-shaped or oval, and is more preferably approximately spherical. It preferably contains smooth surfaces, except for the inlet for reagents, and it preferably contains no protruding devices, baffles or impellers.

The propylene and halogen may be mixed in the CSTR zone or before they enter the CSTR zone, as long as they are well micromixed together no later than immediately after their entry into the CSTR zone. Good micromixing can be obtained by intersecting streams of propylene and halogen which have high momentum shear with respect to each other, either in the CSTR zone or in the pipes leading to the CSTR zone. For instance, when propylene and halogen are injected separately into the CSTR zone, the two streams should intersect each other almost immediately after they leave the injection ports. If the reactor does not provide adequate micromixing, large quantities of carbon are produced.

The inlet ports in the CSTR zone preferably do not direct the reagent stream towards the outlet which leads to the plug-flow reactor zone. The angle between the direction of flow at which reagents enter the CSTR zone and the direction of flow at which the reaction mixture leaves the CSTR zone (or the direction of flow into and in the plug-flow reactor zone) is preferably no more than about 90°.

It may also be desirable to feed a minor portion of diluent into the CSTR zone in order to maintain the desired reaction temperature. The diluent is preferably either hydrogen halide or a gas which is inert with respect to the reagents and the reactor vessel under reaction conditions. Examples of suitable inert diluents include nitrogen, helium and the other noble gases. The molar ratio of diluent to reagents in the feed streams is preferably less than 3:1, more preferably less than 2:1, and most preferably less than 1:1. The molar ratio of diluent to reagents in the feed streams may be 0:1, but when diluent is used the ratio is preferably at least 0.01:1, more preferably at least about 0.05:1 and most preferably at least about 0.1:1.

The average residence time in the CSTR zone is preferably selected such that the halogenation reaction is no more than 90 percent completed (as measured by consumption of chlorine, which can be approximated by measuring the temperature rise) in the CSTR zone. The halogenation reaction is preferably at least about 50 percent completed in the CSTR zone, and more preferably at least about 75 percent completed in the CSTR zone. The concentration of unreacted halogen in effluent from the CSTR zone is preferably at least 10 percent of the concentration of chlorine in the reagents injected into the CSTR zone. The concentration of unreacted halogen is more preferably no more than about 50 percent of the concentration in the initial reagents, and most preferably no more than about 25 percent of the concentration in the initial reagents.

Effluent from the CSTR zone flows into a plug-flow reactor zone. The plug-flow reactor zone is preferably a simple tubular reactor. The temperature conditions in the plug-flow reactor zone have the same limitations and preferred embodiments as in the CSTR zone. The residence time in the plug-flow reactor zone is preferably sufficient to consume essentially all of the remaining chlorine in the reaction mixture.

The ratio of volume in the CSTR zone to volume in the total of CSTR zone and plug-flow reactor zone is preferably about 0.1:1 to about 0.9:1, and more preferably about 0.4:1 to about 0.85:1. When the CSTR zone is roughly spherical and the plug-flow reactor zone is a tubular reactor, the ratio of interior diameter of the spherical section to interior diameter of the tubular section is preferably 1.4:1 to 5:1. Effluent from the CSTR zone preferably flows directly into the plug-flow reactor zone without passing through any other pipes or transportation medium, in order to minimize the need to cool and then reheat the reagent.

The total residence time of reagents in the reactor is preferably on average about 0.3 seconds to about 7 seconds. The optimum reaction time varies depending upon the reaction conditions, and can readily be determined by a person of ordinary skill in the art.

Figure 2:
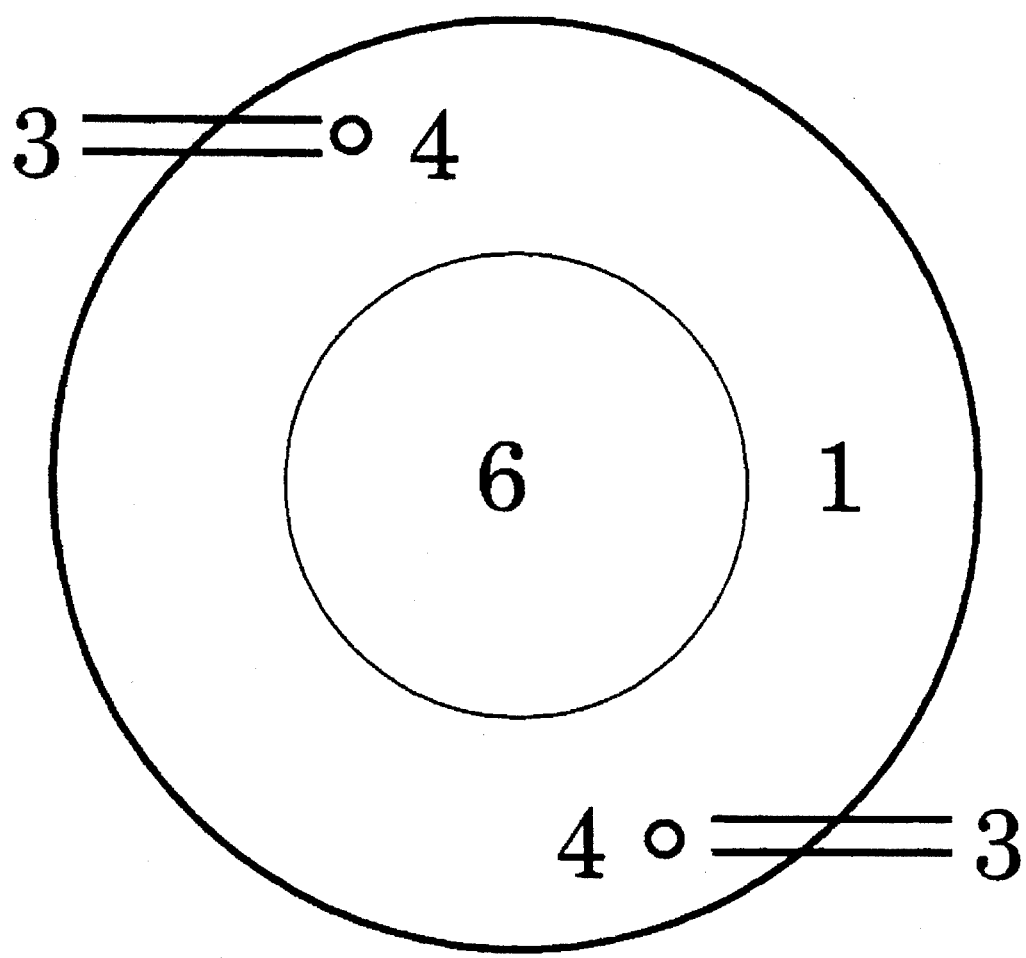
FIG. 2 illustrates a top view of the spherical CSTR zone (1) from the reactor in FIG. 1. It contains: the spherical CSTR zone (1); the inlets for a first reagent (3); the inlets for a second reagent (4); and an opening (6) for the partially-reacted mixture to flow into the plug-flow reactor zone. The illustration shows that the inlets (3) are not pointed directly into the center of the sphere, but enter the reactor directed at an angle from the center.

Referring to the drawings, propylene is injected into a roughly spherical section (1) through lines (3). Injection may be about tangential to the reactor wall or perpendicular to the reactor wall, but is preferably in between those two extremes, as illustrated in FIG. 2. Chlorine is injected into the roughly spherical section (1) through lines (4). The propylene and chlorine streams intersect each other within spherical section (1) almost immediately after they leave the inlets. The streams mix and partially react in the spherical section (1). Effluent from the spherical section flows into the tubular section (2). The effluent still contains a substantial concentration of molecular chlorine. It has a temperature of about 450° C. The chlorine reacts in tubular section (2), until the concentration of molecular chlorine is about zero at the end of the tubular reactor. The product stream is taken out through outlets (5).

Of course, the reactor should be constructed of materials which do not interfere with the reaction or degrade under reaction conditions. Examples of suitable materials include: glass and nickel alloys such as INCONEL nickel-chromium alloy, (produced by International Nickel Co.). The reactor is preferably constructed from INCONEL.

After the removal of unreacted propylene, hydrogen halide and any inert diluent, the product stream preferably contains at least about 80 percent allyl chloride, more preferably at least about 84 percent allyl chloride, more highly preferably at least about 85 percent allyl chloride, and most preferably at least about 86 percent allyl chloride. The product stream preferably contains less than 2 percent dichloropropane, and more preferably less than 1 percent dichloropropane. The product stream preferably contains essentially no molecular chlorine. The concentration of unconsumed molecular chlorine is preferably no more than about 1 weight percent, more preferably no more than about 0.5 weight percent, and most preferably no more than about 0.1 weight percent.

The invention is more specifically illustrated in the following examples.

Illustrative Examples

The following examples are for illustrative purposes only and should not be taken as limiting the scope of either the specification or the claims. Unless otherwise stated, all parts and percentages are by moles.

Examples 1–4

Two glass reactors are made having a roughly spherical CSTR zone and a tubular plug-flow reactor zone in the dimensions shown in Table 1. The spherical CSTR zones each have 0.5 mm diameter nozzles for injecting propylene and 0.5 mm diameter nozzles for injecting chlorine, arranged so the the reagent streams strike each other immediately after entering the reactor. The number of feed nozzle pairs is listed in Table 1.

Propylene, chlorine and helium (as a diluent) are injected into the reactor at the rate shown in Table 1. The helium is injected through the chlorine feed port simultaneously with the chlorine. Propylene is preheated to the temperature shown in Table 1. The reactors are heated and insulated to maintain the desired reaction temperature. The residence time and reactor temperature are shown in Table 1. The products are recovered and analyzed by gas chromatography (GC) analysis using a Hewlett Packard 5890 instrument with a J & W Scientific DB-1 column. The mixture of products is shown in Table 1.

TABLE 1

| | Example | | | |
|---|---|---|---|---|
| | 1 | 2 | 3 | 4 |
| Sphere Vol (CC) | 200.0 | 200.0 | 122.0 | 122.0 |
| Total Vol | 350.0 | 350.0 | 153.0 | 153.0 |
| Sphere ID/Tub. ID* | 1.8 | 1.8 | 5.0 | 5.0 |
| Feed nozzles (pairs) | 4.0 | 4.0 | 1.0 | 1.0 |
| P (abs. atm) | 1.0 | 1.0 | 1.0 | 1.0 |
| Propylene (SCCM)** | 1383.0 | 1383.0 | 1867.0 | 1383.0 |
| Cl2 (SCCM)** | 346.0 | 461.0 | 467.0 | 461.0 |
| He(SCCM)** | 487.0 | 485.9 | 779.0 | 50.0 |
| Reactant preheat (°C.) | 311.0 | 163.1 | 306.3 | 205.6 |
| Pr/Cl2 molar ratio | 4.0 | 3.0 | 4.0 | 3.0 |
| Res. time (s) | 3.7 | 3.8 | 0.8 | 1.8 |
| Reactor Temp. (°C.) | 489.1 | 444.4 | 503.5 | 502.5 |
| % selectivity*** | | | | |
| allyl chloride | 84.06 | 84.49 | 86.44 | 85.25 |
| dichloropropane | 0.19 | 0.84 | 0.49 | 0.30 |
| cis-1,3-dichloropropene | 2.61 | 3.49 | 2.16 | 2.82 |
| trans-1,3-dichloropropene | 2.16 | 2.65 | 1.64 | 2.14 |
| 2-chloropropene | 2.40 | 2.64 | 3.01 | 2.54 |
| Unknown | 3.80 | 2.01 | 1.94 | 2.34 |
| Others | 4.78 | 3.88 | 4.33 | 4.61 |

*ID = Internal diameter
**SCCM = standard cubic centimeters per minute
***% Selectivity is based upon moles of propylene converted

What is claimed is:

1. A process to make an allyl halide wherein the halide is selected from the group consisting of chloride and bromide comprising the steps of:

(1) initially reacting propylene and molecular halogen selected from the group consisting of chlorine and bromine in a molar ratio of at least about 2.5:1 in a continuously stirred tank reactor (CSTR) zone under conditions suitable to provide a reaction temperature of about 400° C. to 525° C. to partially convert propylene and said molecular halogen into allyl chloride; and (2) feeding an effluent from Step (1) into a plug-flow reactor zone where the reaction is continued at a temperature of about 400° C. to 525° C. until essentially all of said halogen is consumed.

2. The process of claim 1 wherein the molecular halogen is chlorine.

3. The process of claim 2 wherein the CSTR zone is roughly spherical, oval or egg-shaped, and the plug-flow reactor zone is roughly tubular.

4. The process of claim 3 wherein the ratio of volume in the CSTR zone to volume in the total of CSTR zone and plug-flow reactor zone is about 0.1:1 to about 0.4:1.

5. The process of claim 4 wherein the molar ratio of propylene to halogen fed into the reactor is no more than about 5:1.

6. The process of claim 4 wherein the temperature in the CSTR zone is about 425° C. to 500° C.

7. The process of claim 4 wherein the ratio of volume in the CSTR zone to volume in the total of CSTR zone and plug-flow reactor zone is about 0.4:1 to about 0.85:1.

8. The process of claim 4 wherein the concentration range of unreacted chlorine in effluent leaving the CSTR zone is about 10 to about 50 percent of the concentration in the initial reagents.

9. The process of claim 4 wherein the concentration range of unreacted chlorine in effluent leaving the CSTR zone is about 10 to about 25 percent of the concentration in the initial reagents.

10. The process of claim 4 wherein the total residence time of reagents in the reactor is on average about 0.3 seconds to about 7 seconds.

11. The process of claim 4 wherein a diluent is injected into the reactor.

12. The process of claim 4 wherein the propylene and molecular halogen are injected into the reactor by separate streams which strike each other within the reactor after they leave their respective feed ports.

13. The process according to claim 4 wherein the propylene and chlorine are mixed before they are injected into the reactor.

14. The process of claim 4 wherein the product stream contains at least about 85 weight percent allyl chloride, after removal of diluent, hydrogen halide and unreacted propylene.

* * * * *

UNITED STATES PATENT AND TRADEMARK OFFICE
CERTIFICATE OF CORRECTION

PATENT NO. : 5,504,266
DATED : April 2, 1996
INVENTOR(S) : Max M. Tirtowidjojo; Paul C. Beckett; John F. Baker It is certified that error appears in the above-identified patent and that said Letters Patent is hereby corrected as shown below:

Claim 1, column 6, line 39, "allyl chloride" should correctly read --said allyl halide--

Signed and Sealed this

Sixteenth Day of March, 1999

Attest:

Q. TODD DICKINSON

Attesting Officer

Acting Commissioner of Patents and Trademarks